United States Patent
Ogihara et al.

[11] Patent Number: 5,560,866
[45] Date of Patent: Oct. 1, 1996

[54] PROCESS FOR PREPARING SILACYCLOHEXANE COMPOUNDS

[75] Inventors: Tsutomu Ogihara; Takaaki Shimizu; Takeshi Kinsho; Tatsushi Kaneko; Mutsuo Nakashima, all of Niigata-ken, Japan

[73] Assignee: Shin-Etsu Chemical Co., Ltd., Tokyo, Japan

[21] Appl. No.: 491,141

[22] Filed: Jun. 16, 1995

[30] Foreign Application Priority Data

Jun. 22, 1994 [JP] Japan .................... 6-163065

[51] Int. Cl.$^6$ .................... C09K 19/34; C09K 19/30; C07F 7/08
[52] U.S. Cl. .................... 252/299.61; 252/299.66; 252/299.63; 556/406; 556/477
[58] Field of Search .................... 252/299.1, 299.61, 252/299.63, 299.66; 428/1; 556/406, 477

[56] References Cited

U.S. PATENT DOCUMENTS

| | | | |
|---|---|---|---|
| 4,410,570 | 10/1983 | Kreuger et al. | 428/1 |
| 5,454,977 | 10/1995 | Shimizu et al. | 252/299.61 |

FOREIGN PATENT DOCUMENTS

| | | |
|---|---|---|
| 648773 | 4/1995 | European Pat. Off. . |
| 682031 | 11/1995 | European Pat. Off. . |
| 7-112990 | 5/1995 | Japan . |

*Primary Examiner*—Shean C. Wu
*Attorney, Agent, or Firm*—Lowe, Price, LeBlanc & Becker

[57] ABSTRACT

A process for preparing a silacyclohexane compound of the general formula

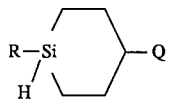

wherein R and Q are, respectively, defined substituents, which process comprising the steps of converting a compound of the following formula

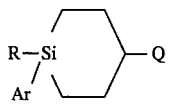

to a halosilacyclohexane of the following formula

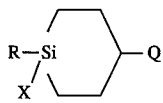

wherein X is a halogen, reacting the halosilacyclohexane with an alcohol to obtain an alkoxysilacyclohexane of the formula which is equilibrated in steric configuration, and

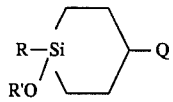

reducing the equilibrated alkoxysilacyclohexane whereby a trans form silacyclohexane compound is predominantly produced.

5 Claims, No Drawings

PROCESS FOR PREPARING SILACYCLOHEXANE COMPOUNDS

BACKGROUND OF THE INVENTION

1. Field of The Invention

This invention relates to a process for preparing silacyclohexane compounds which are useful as liquid crystal substance for liquid crystal display devices.

2. Description of the Prior Art

The liquid crystal display devices make use of optical anisotropy and dielectric anisotropy of liquid crystal substances. Depending on the mode of display, a variety of display systems are known including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

Although the properties of the liquid substances used in these liquid crystal devices depend, more or less, on the type of display, it is commonly required that the liquid crystal substances have a wide range of liquid crystal working temperatures and that they are stable against moisture, air, light, heat, electric field and the like. Moreover, the liquid crystal substances should desirably be low in viscosity and should ensure a short address time, a low threshold voltage and a high contrast in cells.

As the liquid crystal display devices have wider utility in recent years, the characteristic properties required for liquid crystal materials become much severer. In addition, those characteristics which have never been required for conventional liquid crystal substances are now expected such as a lower drive voltage, a wider working temperature range which could satisfy on-vehicle needs and an improvement in low temperature performance.

Under these circumstances, we developed novel liquid crystal compounds which contain a silicon atom in the molecule so that the characteristic properties for use as a liquid crystal substance are improved, and proposed such liquid crystal compounds and preparation thereof in our earlier Japanese Patent Applications as will be set out hereinafter. As liquid crystals compounds, a trans form is useful. The liquid crystal compounds which we developed are obtained as a mixture of cis and trans forms. Although the mixture may be used in liquid crystal display devices, usual practice is to separate the trans form compound from the mixture.

SUMMARY OF THE INVENTION

It is an object of the invention to provide a process for preferentially, selectively preparing trans-form silacyclohexane compounds for use as a liquid crystal substance.

The above object can be achieved, according to the invention, by a process which comprises the steps of:
subjecting a compound of the following general formula (1)

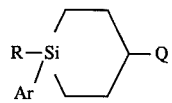

wherein Ar represents a phenyl group or tolyl group, R represents a linear alkyl group having from 1 to 10 carbon atoms, a branched alkyl group having from 3 to 8 carbon atoms, a mono or difluoroalkyl group having from 1 to 10 carbon atoms, or an alkoxyalkyl group having from 2 to 7 carbon atoms, and Q represents a group of the following general formula (2)

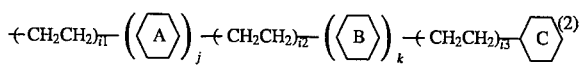

wherein $-\langle A \rangle-$ and $-\langle B \rangle-$ independently represent

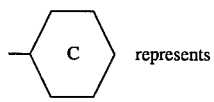

in which Y represents H, F or methyl and $l$ is a value of 0, 1 or 2, and $-\langle C \rangle-$ represents

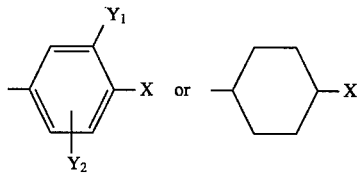

in which each X represents CN, F, Cl, $CF_3$, $CF_2Cl$, $OCF_3$, $OCHF_2$, $OCF_2Cl$, $OCHFCl$, $(O)_m CY_3 = CX_1 X_2$ wherein $m$ is 0 or 1, $Y_3$ and $X_1$ independently represent H, F or Cl, $X_2$ represents F or Cl, $O(CH_2)_r(CF_2)_s X_3$ wherein $r$ and $s$ are, respectively, a value of 0, 1 or 2 provided that $r+s=2$, 3 or 4, $X_3$ represents F or Cl, or R or OR wherein R has the same meaning as defined above, i1, i2 and i3 are, respectively, a value of 0 or 1 provided that $i1+i2+i3=1$, and $j$ and $k$ are, respectively, a value of 0, 1 or 2 provided that $j+k=0$, 1 or 2, $Y_1$ and $Y_2$ independently represent H, F or Cl, to reaction with an electrophilic reagent for conversion into a halosilacyclohexane compound of the following general formula (3)

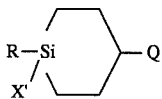

wherein R and Q have, respectively, the same meanings as defined above, and X' represents, F, Cl, Br or I;
further reacting the halosilacyclohexane compound with an alcohol of the general formula, R'OH, wherein R' represents a linear alkyl group having from 1 to 10 carbon atoms or a branched alkyl group having from 3 to 8 carbon atoms to obtain an alkoxysilacyclohexane of the following general formula (4) wherein the steric configuration of the group, R, is equilibrated on the silicon atom

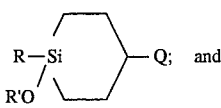  (4)

subjecting the alkoxysilacyclohexane to reduction to obtain a silacyclohexane compound of the following general formula (5)

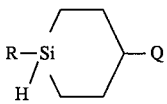  (5)

DETAILED DESCRIPTION OF THE INVENTION

In the process of preparing known hydrocarbon liquid crystal compounds, it is known that cis-form compounds which do not exhibit any liquid crystal properties, are inevitably, secondarily produced along with trans-form compounds exhibiting liquid crystal properties. In order to reduce a loss from the standpoint of the preparation of the compounds, it is desirable to selectively produce trans-form compounds as much as possible. The selective and predominant preparation of trans-form liquid crystal compounds has never been hitherto reported yet.

The invention contemplates to prepare silicon-containing liquid crystal compounds wherein trans-form compounds which are necessary for practical applications are preferentially prepared. The reactions through which high steric selectivity is attained are considered as impossible for the preparation of known hydrocarbon liquid crystal compounds. Nevertheless, with novel types of liquid crystal compounds containing a silicon atom in the molecule as proposed in our earlier Japanese Patent Applications which have not laid open yet, the selective preparation of trans-form compounds is possible. This eventually leads to an improved yield as a whole of the production process and is better in economy than in the case of known hydrocarbon liquid crystal compounds.

The process of the invention is described. In the process, a phenyl or tolylsilacyclohexane of the following general formula (1) is first provided

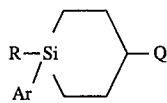  (1)

wherein Ar represents a phenyl group or a tolyl group, R represents a linear alkyl group having from 1 to 10 carbon atoms, a branched alkyl group having from 3 to 8 carbon atoms, a mono or difluoroalkyl group having from 1 to 10 carbon atoms, or an alkoxyalkyl group having from 2 to 7 carbon atoms, and Q represents a group of the afore-indicated general formula (2)

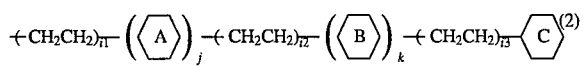  (2)

wherein 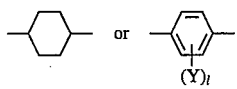 independently represents in which Y represents H, F or methyl and l is a value of 0, 1 or 2, and

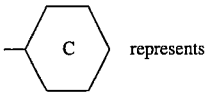 represents

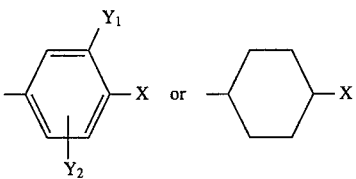

in which each X represents CN, F, Cl, $CF_3$, $CF_2Cl$, $OCF_3$, $OCHF_2$, $OCF_2Cl$, $OCHFCl$, $(O)_mCY_3=CX_1X_2$ wherein m is 0 or 1, $Y_3$ and $X_1$ independently represent H, F or Cl, $X_2$ represents F or Cl, $O(CH_2)_r(CF_2)_sX_3$ wherein r and s are, respectively, a value of 0, 1 or 2 provided that r+s=2, 3 or 4, $X_3$ represents F or Cl, or R or OR wherein R has the same meaning as defined above, i1, i2 and i3 are, respectively, a value of 0 or 1 provided that i1+i2+i3=1, and j and k are, respectively, a value of 0, 1 or 2 provided that j+k=0,1 or 2, $Y_1$ and $Y_2$ independently represent H, F or Cl.

In the formula (1), specific examples of the linear alkyl group having from 1 to 10 carbon represented by R include methyl, ethyl, n-propyl, n-butyl, n-pentyl, n-hexyl, n-heptyl, n-octyl, n-nonyl and n-decyl. Specific examples of the mono or difluoroalkyl group having from 1 to 10 carbon atoms include fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl and 10,10-difluorodecyl.

Specific examples of the branched alkyl group having 3 to 8 carbon atoms include isopropyl, 1-methylpropyl, 2-methylpropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Specific examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl and ethoxypentyl.

Of these, preferred linear alkyl groups are ones having from 3 to 7 carbon atoms and include, for example, n-propyl, n-butyl, n-pentyl, n-hexyl and n-heptyl. Likewise, preferred mono or difluoroalkyl groups include 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoroheptyl, 6-fluorohexyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl.

Preferred branched alkyl groups include, for example, isopropyl, 1-methylpentyl, 2-methylpentyl, 1-methylbutyl, 2-methylbutyl, 3-methylbutyl, 1-methylpentyl and 2-ethylhexyl.

Preferred alkoxyalkyl groups include methoxymethyl, methoxyethyl, methoxypropyl, methoxypentyl, ethoxymethyl, ethoxyethyl, propoxymethyl and pentoxymethyl.

The preparation of the compound of the formula (1) has been set out in our Japanese Patent Applications and is particularly described in Preparatory Examples appearing hereinafter. It will be noted here that the earlier Japanese Patent Applications include Japanese Patent Application No. 6-56565, filed Mar. 1, 1994 (refiled as a domestic priority-claiming application No. 7-66982, filed Feb. 28, 1995), Japanese Patent Application No. 6-139497, filed May 30, 1994, Japanese Patent Application No. 6-332082, filed Dec. 12, 1994, Japanese Patent Application No. 6-90495, filed Apr. 5, 1994 (refiled as a domestic priority-claiming application No. 7-101698, filed Apr. 3, 1995), Japanese Patent Application No. 6-115872, filed May 2, 1994 (refiled as a domestic priority-claiming application No. 7-123067, filed Apr. 24, 1995), Japanese Patent Application No. 6-154220, filed Jun. 13, 1994 and Japanese Patent Application No. 6-197895, filed Jul. 29, 1994. These applications have not been laid open yet.

According to the process of the invention, the compound of the formula (1) is converted into a corresponding halosilacyclohexane compound by reaction with an electrophilic reagent according to the following general formula (6)

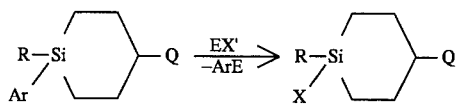

wherein EX' represents an electrophilic reagent, and X' represents a halogen and preferably Cl, I or Br. It will be noted that the de-silylation reaction of the formula (6) may be effected in a wide range of temperatures. The reaction temperature is preferably in the range of from 0° to 80° C., more preferably from 10° to 40° C. The electrophilic reagent is preferably used at a ratio by mole between the silacyclohexane compound and the electrophilic reagent of 1:1 to 1:2.

The electrophilic reagents include, for example, halogens, hydrogen halides, metal halides, sulfonic derivatives, acid halides, alkyl halides and the like. Preferable examples include iodine, bromine, chlorine, iodine monochloride, hydrogen chloride, hydrogen bromide, hydrogen iodide, mercury (II) chloride, trimethysilyl chlorosulfonate, acetyl chloride, acetyl bromide, benzoyl chloride, t-butyl chloride and the like. In order to increase the reaction velocity, addition of Lewis acids such as aluminium chloride, zinc chloride, titanium tetrachloride, boron trifluoride and the like or irradiation of visible light or UV light is effective.

At the time of this reaction, the steric configuration of the group represented by R is equilibrated on the silicon atom in such a way that the groups of R and Q are predominantly in more stable trans position with respect to the silacyclohexane ring. This is particularly shown below

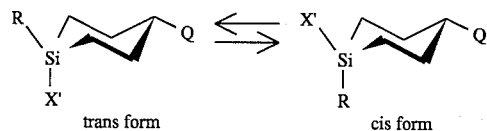

trans form          cis form

It is generally accepted that chlorosilanes undergo reduction when sterically inversed ("The Chemistry of Organic Silicon Compounds Part I, Chapter 4, Saul Patai and Zvi Tappoport; John Wiley & Sons (1989)). This is schematically shown below

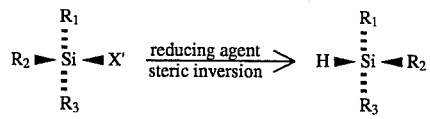

wherein X' is a halogen and $R_1$, $R_2$ and $R_3$ are, respectively, an appropriate alkyl group, for example.

Accordingly, when the halosilacyclohexane compound is reduced by means of a reducing agent of the type set forth hereinafter, the reduction proceeds through the steric inversion, thus resulting in a reduced yield of an intended trans isomer as shown below

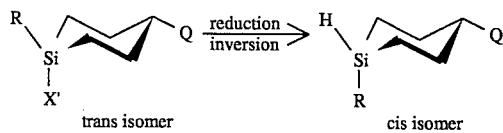

trans isomer          cis isomer

Accordingly, an alkoxysilacyclohexane compound which is reducible while keeping the steric configuration is formed, through which the group of R is caused to be equilibrated on the silicon atom with respect to the steric configuration, permitting the trans isomer to become higher in ratio. Thereafter, the reduction is affected to obtain the intended trans isomer at a higher yield.

The alkoxysilacyclohexane compound which should be essentially formed in the process of the invention can be obtained by reaction between the halosilacyclohexane compound and an alcohol according to the following reaction formula (7)

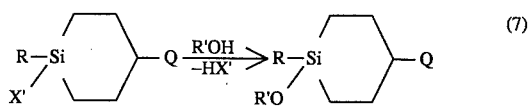

wherein X', R and Q have, respectively, the same meanings as defined before, and R' represents a linear alkyl group having from 1 to 10 carbon atoms or a branched alkyl group having from 3 to 8.

During the reaction between the halosilacyclohexane compound and the alcohol, the steric configuration of the group of R is equilibrated on the silicon atom, thereby permitting the groups of Q and R to be in more stable trans configuration as shown below

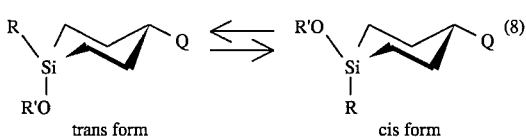

trans form     cis form     (8)

It is known that alkoxysilanes undergo reduction while keeping the steric configuration ("The Chemistry of Organic Silicon Compounds Part I, Chapter 4, Saul Patai and Zvi Tappoport; John Wiley & Sons (1989)) as shown below

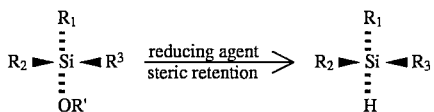

Accordingly, when the alkoxysilacyclohexane compound is reduced with a reducing agent, the reduction proceeds while keeping the steric configuration, thereby obtaining an intended trans isomer in high yield. This is shown in the following formula (9)

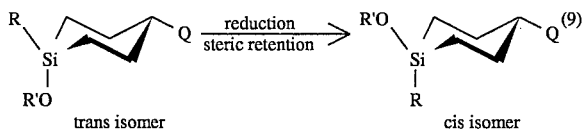

trans isomer     cis isomer

The alcohol used in the formula (7) is one which has a linear or branched alkyl moiety having from 1 to 10 carbon atoms. Examples of the linear or branched alkyl moiety or group include those defined with respect to R in the formula (1). In order to neutralize the hydrogen halide generated during the reaction between the halosilacyclohexane compound and the alcohol, amines such as triethylamine, urea and the like and epoxy compounds such as propylene oxide may be added.

The equilibration takes place on the conversion of the halosilacyclohexane compound to a corresponding alkoxysilacyclohexane compound as shown in the formula (8). The reaction is effected preferably under conditions of a temperature ranging from 0° to 80° C. and a time ranging from 0.1 to 5 hours. In this connection, the equilibration is facilitated by heating the reaction system to a temperature of from 30° to 80° C. Accordingly, this temperature range is more preferably used. Alternatively, the equilibration may also be facilitated when lower alcohols are added to the reaction system in amounts of 1 to 5 equivalents based on the starting halosilacyclohexane compound. The lower alcohols are those which have from 1 to 5 carbon atoms and include, for example, methanol, ethanol, n-propyl alcohol, iso-propyl alcohol, n-butyl alcohol and the like. Still alternatively, metal alcoholates such as methyl alcoholate, ethyl alcoholate and the like may be used for promoting the equilibration. The metal alcoholates may be used in such amounts as with the lower alcohol.

The equilibrated alkoxysilacyclohexane compound is then reduced with a reducing agent to obtain a silacyclohexane compound. Examples of such a reducing agent include metal hydrides such as sodium hydride, potassium hydride, trialkylsilanes, boranes, dialkyl aluminium compounds and the like, complex hydrides such as lithium aluminohydride, sodium borohydride, lithium borohydride, potassium borohydride, tributylammonium borohydride and the like, and substituted hydrides thereof such as lithium trialkoxyaluminohydride, sodium di(methoxyethoxy)aluminohydride, lithium triethylborohydride, sodium cyanoborohydride and the like. The reducing agent is preferably used in amounts of from 1 to 5 equivalents based on the alkoxysilacyclohexane.

Although not limitative, the reduction of the halosilacyclohexane is carried out preferably at a temperature of from 0° to 100° C., more preferably from 20° to 70° C.

In the steps set out hereinabove, the reactions are usually carried out in solvents inert to the respective reactants. Examples of the solvent include ethers such as diethyl ether, tetrahydrofuran, dioxane and the like, lower alcohols having from 1 to 5 carbon atoms, and hydrocarbons such as benzene, toluene, xylene, hexane, iso-octane and the like.

The silacyclohexane compounds prepared according to the process of the invention may be subsequently purified to a level necessary for practical applications by a usual manner such as recrystallization or chromatography, thereby obtaining an intended trans isomer of silacyclohexane compound. This trans isomer is useful as a liquid crystal substance.

When comparing with the process for preparing hitherto known hydrocarbon liquid compounds, the process of the invention is higher in selectivity to a trans isomer of silicon-containing silacyclohexane compound. This is considered very valuable from the standpoint of industrial preparation of the compound in the sense that a production loss caused by the secondary formation of a cis isomer in the production process is significantly reduced.

The invention is more particularly described by way of examples.

Preparatory Example 1

Preparation of
4-(trans-4-(2-(3,4-difluorophenyl)ethyl)cyclohexyl)-
1-n-pentyl-1-phenyl-1-silacyclohexane 12.0 g of potassium t-butoxide was added to a mixture of 47.0 g of 3,4-difluorobenzyltriphenylphosphonium bromide and 200 ml of tetrahydrofuran (hereinafter referred to as THF) to obtain an orange-colored ylide solution. 50 ml of a THF solution of 35.0 g of 4-(4-n-pentyl-4-phenyl-4-silacyclohexyl)cyclohexane carbaldehyde was added to the solution, followed by agitation at room temperature for 2 hours. Thereafter, the reaction solution was poured into iced water and extracted with ethyl acetate. The resultant extract was washed with brine, dried and concentrated to obtain a residue, to which 100 ml of n-hexane was added. The resultant crystals of triphenylphosphine oxide were separated by filtration and the resultant filtrate was concentrated. The resultant residue was purified through silica gel chromatography to obtain 41.7 g of 4-(trans-4-(2-(3,4-difluorophenyl)ethenyl)cyclohexyl)-1-n-pentyl-1-phenyl-1-silacyclohexane. This product was subjected to IR analysis with the results shown below.

IR (liquid film) $v_{max}$: 2920, 2855, 1595, 1515, 1425, 1290, 1110, 960, 800 cm$^{-1}$ 40.0 g of the thus obtained 4-(trans-4-(2-(3,4-difluorophenyl)ethenyl)cyclohexyl)-1-n-pentyl-1-phenyl-1-silacyclohexane was dissolved in 200 ml of ethyl acetate and hydrogenated in the presence of 200 mg of platinum oxide at a pressure of 0.1 MPa of hydrogen. After theoretical consumption of hydrogen, the catalyst was removed by filtration and the resultant filtrate was concentrated to obtain 40.2 g of 4-(trans-4-(2-(3,4-difluorophenyl)ethyl)cyclohexyl)-1-n-pentyl-1-phenyl-1-silacyclohexane. The results of IR analysis of the product are as follows.

IR (liquid film) $v_{max}$: 2920, 2855, 1605, 1518, 1280, 1110, 853, 810 cm$^{-1}$

EXAMPLE 1

Preparation of
trans-4-(trans-4-(2-(3,4-difluorophenyl)ethyl)
cyclohexyl)-1-n-pentyl-1-silacyclohexane 100 ml of a dichloromethane solution of 1.0 mole/liter of iodine monochloride was added to 40.0 g of 4-(trans-4-(2-(3,4-difluorophenyl)ethyl)cyclohexyl)-1-n-pentyl-1-phenyl-1-silacyclohexane obtained in Preparatory Example 1 at room temperature, followed by agitation for 1 hour to obtain a cis-trans isomer mixture. The results of GC-MS analysis are shown below. GC-MS (70 eV)(m/z)$^+$ Cis isomer: 426 ($M^+$), 355 ($M^+$—$C_5H_{11}$) Trans isomer: 426 ($M^+$), 355 ($M^+$—$C_5H_{11}$)

Thereafter, a mixture of 4.0 g of methanol and 11.0 g of triethylamine was added to the solution at room temperature, followed by further agitation under reflux for 1 hour. The resultant cis-trans isomer mixture of 4-(trans-4-(2-(3,4-difluorophenyl)ethyl)cyclohexyl)-1-n-pentyl-1-methoxy-1-silacyclohexane was subjected to quantitative analysis through gas chromatography, with the result that a ratio of a cis isomer (retention time: 12.02 minutes) and a trans isomer (retention time: 12.28 minutes) was found to be 10:90.

The gas-chromatographic measuring apparatus used was Model 5890-II made by Hewlett Packard company with a capillary column of Ultra-20 of Hewlett Packard company having a size of 0.25ϕ×30 m. In ensuing examples, these apparatus and capillary column were also used. The temperature conditions were those wherein the mixture was heated from 200° C. up to 300° C. at a rate of 10° C./minute. The results of the GC-MS analysis of the mixture are shown below. GC-MS (70 eV) (m/z)$^+$ Cis isomer: 422 ($M^+$), 351 ($M^+$—$C_5H_{11}$) Trans isomer: 422 ($M^+$), 351 ($M^+$—$C_5H_{11}$)

Subsequently, the reaction mixture was concentrated, to which 200 ml of hexane was added thereby permitting secondarily produced triethylamine hydrochloride to be precipitated, followed by removal by filtration. The resultant filtrate was concentrated to obtain 34.6 g of 4-(trans-4-(2-(3,4-difluorophenyl)ethyl)cyclohexyl)-1-n-pentyl-1-methoxy-1-silacyclohexane. This silacyclohexane product was dissolved in 100 ml of THF and was added to 100 ml of a THF solution of 10.0 g of lithium aluminohydride, followed by agitation under reflux for 1 hour. The cis-trans isomer mixture was subjected to quantitative gas-chromatographic analysis in the same manner as set out hereinabove, revealing that a ratio of the cis isomer (retention time: 11.35 minutes) and the trans isomer (retention time: 11.61 minutes) was 12:88. The reaction mixture was poured into 200 ml of 5% hydrochloric acid and extracted with ethyl acetate. The extract was subjected to ordinary procedures of washing with brine, drying and concentration, followed by purification through silica gel chromatography to obtain 28.9 g of an intended product (yield: 86.3%). This product exhibited nematic liquid crystal properties at a temperature between 7.6° and 69.7° C. and was found to be very useful as a liquid crystal substance. The results of IR analysis of the product are shown below.

IR (liquid film) $v_{max}$: 2920, 2852, 2098, 1520, 1286, 1211, 1119, 887, 816 cm$^{-1}$

Comparative Example 1

100 ml of a dichloromethane solution of 1.0 mole/liter of iodine monochloride was added to 40.0 g of 4-(trans-4-(2-(3,4-difluorophenyl)ethyl)cyclohexyl)-1-n-pentyl-1-phenyl-1-silacyclohexane obtained in Preparatory Example 1 at room temperature, followed by agitation for 1 hour to obtain a cis-trans isomer mixture. The mixture was subjected to quantitative gas-chromatographic analysis in the same manner as in Example 1, revealing that a ratio between the cis isomer (retention time: 12.62 minutes) and the trans isomer (retention time: 13.05 minutes) was 83.17. The reaction mixture was concentrated, after which the resultant residue was dissolved in 100 ml of THF and added to 100 ml of a THF solution of 10.0 g of lithium aluminohydride at 0° C. The reaction mixture was agitated for 30 minutes, followed by quantitative gas-chromatographic analysis in the same manner as in Example 1, with the result that a ratio between the cis isomer and the trans isomer was 83:17. The reaction mixture was poured into 200 ml of 5% hydrochloric acid and extracted with ethyl acetate. The resultant extract was subjected to ordinary procedures of washing with brine, drying and concentration, followed by purification through silica gel chromatography to obtain 5.4 g (yield: 16.1%) of the intended product.

Preparatory Example 2

Preparation of
4-(trans-4-(3,4-difluorophenyl)cyclohexyl)-
1-n-pentyl-1-phenyl-1-silacyclohexane 19.3 g of 3,4-difluorobromobenzene was dropped in a mixture of 2.55 g of magnesium and 50 ml of THF, followed by refluxing for 3 hours to obtain a Grignard reagent and further addition of 50 ml of a THF solution of 34.0 g of 4-4(n-pentyl-4-phenyl-4-silacyclohexyl)cyclohexanone.

After refluxing for 2 hours, the reaction mixture was cooled down to room temperature and poured into an ammonium chloride aqueous solution, followed by extraction with benzene. 1 g of p-toluenesulfonic acid was added to the resultant benzene solution, followed by separation and removal of the resultant water under reflux. At the time when any water was not distilled off, the reaction mixture was cooled down to room temperature. Thereafter, the reaction mixture was charged into a sodium hydrogencarbonate aqueous solution, followed by ordinarily washing with brine, drying and concentration. The resultant residue was purified through silica gel chromatography to obtain 38.0 g of 4-(4-(3,4-difluorophenyl)-3-cyclohexenyl)-1-n-pentyl-1-phenyl-1-silacyclohexane. This product was dissolved in 200 ml of ethyl acetate and subjected to hydrogenation at a pressure of hydrogen of 0.5 MPa in the presence of 200 mg of a palladium-carbon catalyst. After theoretical consumption of hydrogen, the catalyst was removed by filtration and the resultant filtrate was concentrated to obtain 38.2 g of 4-(trans-4-(3,4-difluorophenyl)cyclohexyl)-1-n-pentyl-1-phenyl-1-silacyclohexane. The results of IR analysis of the product are shown below.

IR (liquid film) $v_{max}$: 2920, 2855, 1603, 1517, 1422, 1274, 1110, 868, 812 cm$^{-1}$

EXAMPLE 2

Preparation of
trans-4-(trans-4-(3,4-difluorophenyl)cyclohexyl)-
1-n-pentyl-1-silacyclohexane 100 ml of a dichloromethane solution of 1.0 mole/liter of iodine monochloride was added to 38.0 g of 4-(trans-4-(3, 4-difluorophenyl)cyclohexyl)-1-n-pentyl-1-phenyl-1-silacyclohexane obtained in Preparatory Example 2 at room temperature, followed by agitation for 1 hour to obtain a cis-trans isomer mixture. The results of GC-MS analysis are shown below. GC-MS (70 eV) (m/z)$^+$ Cis isomer: 398 (M$^+$), 327 (M$^+$—C$_5$H$_{11}$) Trans isomer: 398 (M$^+$), 327 (M$^+$—C$_5$H$_{11}$)

Thereafter, a mixture of 5.0 g of ethanol and 6.0 g of urea was added to the solution at room temperature, followed by further agitation under reflux for 1 hour. The resultant cis-trans isomer mixture of 4-(trans-4-(3,4-difluorophenyl)cyclohexyl)-1-n-pentyl-1-ethoxy-1-silacyclohexane was subjected to quantitative analysis through gas chromatography, with the result that a ratio of the cis isomer (retention time: 10.65 minutes) and the trans isomer (retention time: 10.72 minutes) was found to be 10:90.

The results of the GC-MS analysis of the mixture are shown below. GC-MS (70 eV) (m/z)$^+$ Cis isomer: 408 (M$^+$), 337 (M$^+$—C$_5$H$_{11}$) Trans isomer: 408 (M$^+$), 337 (M$^+$—C$_5$H$_{11}$)

Subsequently, the reaction mixture was concentrated, to which 200 ml of hexane was added thereby permitting secondarily produced urea hydrochloride to be precipitated and separated. The residual solution was concentrated to obtain 33.8 g of 4-(trans-4-(3,4-difluorophenyl)cyclohexyl)-1-n-pentyl-1-ethoxy-1-silacyclohexane. This silacyclohexane product was dissolved in 100 ml of THF and was added to 100 ml of a THF solution of 10.0 g of lithium aluminohydride, followed by agitation under reflux for 1 hour. The cis-trans isomer mixture was subjected to quantitative gas-chromatographic analysis in the same manner as set out in Example 1, revealing that a ratio of the cis isomer (retention time: 9.56 minutes) and the trans isomer (retention time: 9.66 minutes) was 11:89. The reaction mixture was poured into 200 ml of 5% hydrochloric acid and extracted with ethyl acetate. The extract was subjected to ordinary procedures of washing with brine, drying and concentration, followed by purification through silica gel chromatography to obtain 25.2 g of the intended product (yield: 80.2%). This product exhibited nematic liquid crystal properties at a temperature between 14.3° and 71.6° C. and was found to be very useful as a liquid crystal substance. The results of IR analysis of the product are shown below.

IR (liquid film) $v_{max}$: 2923, 2845, 2092, 1608, 1520, 1296, 1213, 1113, 891, 825, 808 cm$^{-1}$ Comparative Example 2

100 ml of a dichloromethane solution of 1.0 mole/liter of iodine monochloride was added to 33.0 g of 4-(trans-4-(3,4-difluorophenyl)cyclohexyl)-1-n-pentyl-1-phenyl-1-silacyclohexane obtained in Preparatory Example 2 at room temperature, followed by agitation for 1 hour to obtain a cis-trans isomer mixture. The mixture was subjected to quantitative gas-chromatographic analysis in the same manner as in Example 1, revealing that a ratio between the cis isomer (retention time: 10.83 minutes) and the trans isomer (retention time: 11.17 minutes) was 84:16. The reaction mixture was concentrated, after which the resultant residue was dissolved in 100 ml of THF and added to 100 ml of a THF solution of 10.0 g of lithium aluminohydride at 0° C. The reaction mixture was agitated for 30 minutes, followed by quantitative gas-chromatographic analysis in the same manner as in Example 1, with the result that a ratio between the cis isomer and the trans isomer was 84:16. The reaction mixture was poured into 200 ml of 5% hydrochloric acid and extracted with ethyl acetate. The resultant extract was subjected to ordinary procedures of washing with brine, drying and concentration, followed by purification through silica gel chromatography to obtain 3.9 g (yield: 12.4%) of the intended product.

Preparatory Example 3

Preparation of 4-(p-fluorophenyl)-1-n-heptyl-1-phenyl-1-silacyclohexane 17.5 g of p-fluorobromobenzene was dropped in a mixture of 2.55 g of magnesium and 50 ml of THF, followed by refluxing for 3 hours to obtain a Grignard reagent. 50 ml of a THF solution of 28.0 g of 4-n-heptyl-4-phenyl-4-silacyclohexanone was further added to the solution. After refluxing for 2 hours, the reaction mixture was cooled down to room temperature and poured into an ammonium chloride aqueous solution, followed by extraction with benzene. 1 g of p-toluenesulfonic acid was added to the resultant benzene solution, followed by separation and removal of the resultant water under reflux. At the time when any water was not distilled off, the reaction mixture was cooled down to room temperature. Thereafter, the reaction mixture was charged into a sodium hydrogencarbonate aqueous solution, followed by ordinarily washing with brine, drying and concentration. The resultant residue was purified through silica gel chromatography to obtain 33.0 g of 4-(p-fluorophenyl)-1-n-heptyl-1-phenyl-1-sila-3-cyclohexene. This product was dissolved in 200 ml of ethanol and subjected to hydrogenation at a pressure of hydrogen of 0.5 MPa in the presence of 200 mg of a palladium-carbon catalyst. After theoretical consumption of hydrogen, the catalyst was removed by filtration and the resultant filtrate was concentrated to obtain 33.2 g of 4-(p-fluorophenyl)-1-n-heptyl-1-phenyl-1-silacyclohexane.

EXAMPLE 3

Preparation of trans-4-(p-fluorophenyl)-1-n-heptyl-1-silacyclohexane 100 ml of a dichloromethane solution of 1.0 mole/liter of iodine monochloride was added to 33.0 g of 4-(p-fluorophenyl)-1-n-heptyl-1-phenyl-1-silacyclohexane obtained in Preparatory Example 3 at room temperature, followed by agitation for 1 hour to obtain a cis-trans isomer mixture. The results of GC-MS analysis are shown below. GC-MS (70 eV) (m/z)$^+$ Cis isomer: 326 (M$^+$), 298 (M$^+$—C$_2$H$_4$), 297 (M$^+$—C$_7$H$_{15}$) Trans isomer: 326 (M$^+$), 298 (M$^+$—C$_2$H$_4$), 297 (M$^+$—C$_7$H$_{15}$)

Thereafter, a mixture of 7.0 g of isopropyl alcohol and 11.0 g of triethylamine was added to the solution at room temperature, followed by further agitation under reflux for 1 hour. The resultant cis-trans isomer mixture of 4-(p-fluorophenyl)-1-n-heptyl-1-isopropoxy-1-silacyclohexane was subjected to quantitative analysis through gas chromatography, with the result that a ratio of the cis isomer (retention time: 6.64 minutes) and the trans isomer (retention time: 6.74 minutes) was found to be 14:86.

The results of the GC-MS analysis of the mixture are shown below. GC-MS (70 eV) (m/z)$^+$ Cis isomer: 350 (M$^+$), 322 (M$^+$—C$_2$H$_4$), 251 (M$^+$—C$_7$H$_{15}$) Trans isomer: 350 (M$^+$), 322 (M$^+$—C$_2$H$_4$), 251 (M$^+$—C$_7$H$_{15}$)

Subsequently, the reaction mixture was concentrated, to which 200 ml of hexane was added thereby permitting secondarily produced triethylamine hydrochloride to be precipitated and separated by filtration. The resultant filtrate was concentrated to obtain 28.2 g of 4-(p-fluorophenyl)-1- n-heptyl-1-isopropoxy-1-silacyclohexane. This silacyclohexane product was dissolved in 100 ml of THF and was added to 100 ml of a THF solution of 10.9 g of lithium aluminohydride, followed by agitation under reflux for 2 hours. The cis-trans isomer mixture was subjected to quantitative gas-chromatographic analysis in the same manner as set out in Example 1, revealing that a ratio of the cis isomer (retention time: 5.65 minutes) and the trans isomer (retention time: 5.71 minutes) was 15.85. The reaction mixture was poured into 200 ml of 5% hydrochloric acid and extracted with ethyl acetate. The extract was subjected to ordinary procedures of washing with brine, drying and concentration, followed by purification through silica gel chromatography to obtain 19.0 g of the intended product (yield: 72.6%). The result of IR and $^{13}$C-NMR analysis of the product are shown below.

IR (liquid film) $v_{max}$:2920, 2100, 1510, 1458, 1408, 1228, 985, 887, 820 cm$^{-1}$ $^{13}$C-NMR (67.5 MHz, CDCl$_3$); 10.56 (s), 12.13 (s), 14.11 (s), 22.74 (s), 24.44 (s), 29.08 (s), 31.85 (s), 33.19 (s), 33.45 (s), 46.92 (s), 114.90 (d), 127.89 (d), 144.31 (d), 161.09 (d) ppm Comparative Example 3

100 ml of a dichloromethane solution of 1.0 mole/liter of iodine monochloride was added to 33.0 g of 4-(p-fluorophenyl)-1-n-heptyl-1-phenyl-1-silacyclohexane obtained in Preparatory Example 3 at room temperature, followed by agitation for 1 hour to obtain a cis-trans isomer mixture. The mixture was subjected to quantitative gas-chromatographic analysis in the same manner as in Example 1, revealing that a ratio between the cis isomer (retention time: 6.50 minutes) and the trans isomer (retention time: 6.78 minutes) was 83:17. The reaction mixture was concentrated, after which the resultant residue was dissolved in 100 ml of THF and added to 100 ml of a THF solution of 10.0 g of lithium aluminohydride at 0° C. The reaction mixture was agitated for 30 minutes, followed by quantitative gas-chromatographic analysis in the same manner as in Example 1, with the result that a ratio between the cis isomer and the trans isomer was 80:20. The reaction mixture was poured into 200 ml of 5% hydrochloric acid and extracted with ethyl acetate. The resultant extract was subjected to ordinary procedures of washing with brine, drying and concentration, followed by purification through silica gel chromatography to obtain 5.0 g (yield: 19.2%) of the intended product.

EXAMPLE 4

Preparation of trans-4-(2-(trans-4-(3,4-difluorophenyl)ethyl) cyclohexyl)-1-n-propyl-1-silacyclohexane The general procedure of Example 1 was repeated using 4-(2-(trans-4-(3,4-difluorophenyl)ethyl)cyclohexyl)-1-n-propyl-1-phenyl-1-silacyclohexane. When subjected to gas chromatography under conditions of heating from 200° C. to 300° C. at a rate of 10° C./minute, the resultant product had a retention time of 9.82 minutes for the cis isomer and a retention time of 9.92 minutes for the trans isomer, with a ratio between the cis isomer and the trans isomer of 15.85. The yield was 73.1%. The liquid crystal temperature range was found to be C11.2 N53.5I, i.e. a C—N transition temperature of 11.2° C. and an N—I transition temperature of 53.2° C. The results of IR analysis of the product are shown below.

IR (liquid film) $v_{max}$: 2922, 2850, 2100, 1909, 1518, 1288, 887, 815 cm$^{-1}$ Comparative Example 4

The general procedure of Comparative Example 1 was repeated using (4-(2-(trans-4(3,4-difluorophenyl)ethyl)cyclohexyl)-1-n-propyl-1-phenyl-1-silacyclohexane, thereby obtaining a product as intended in Example 4. The product had a ratio between the cis isomer and the trans isomer of 80:20 at a yield as low as 11.5%, thus being unfavorable.

EXAMPLE 5

Preparation of 4'-(trans-4-n-propyl-4-silacyclohexyl)-4-fluorobiphenyl

The general procedure of Example 1 was repeated using 4'-(4-n-propyl-4-phenyl-4-silacyclohexyl)-4-fluorobiphenyl. When subjected to gas chromatography under conditions of heating from 200° C. to 300° C. at a rate of 10° C./minute, the resultant product had a retention time of 8.64 minutes for the cis isomer and a retention time of 8.78 minutes for the trans isomer, with a ratio between the cis isomer and the trans isomer of 16:84. The yield was 71.6%. The liquid crystal temperature range was found to be C80.2 N119.3I, i.e. a C—N transition temperature of 80.2° C. and an N—I transition temperature of 119.3° C. The results of IR analysis of the product are shown below.

IR (liquid film) $v_{max}$: 2918, 2854, 2087, 1604, 1497, 1238, 987, 889, 816 cm$^{-1}$ Comparative Example 5

The general procedure of Comparative Example 1 was repeated using 4'-(4-n-propyl-4-phenyl-4-silacyclohexyl)-4-fluorobiphenyl, thereby obtaining a product as intended in Example 5. The product had a ratio between the cis isomer and the trans isomer of 79.21 at a yield as low as 13.5%, thus being unfavorable.

EXAMPLE 6

Preparation of trans-4-(2-(p-ethoxyphenyl)ethyl)-1-n-pentyl-1-silacyclohexane

The general procedure of Example 1 was repeated using 4-(2-(p-ethoxyphenyl)ethyl-1-n-pentyl-1-phenyl-silacyclohexane. When subjected to gas chromatography under conditions of heating from 200° C. to 300° C. at a rate of 10° C./minute, the resultant product had a retention time of 7.98 minutes for the cis isomer and a retention time of 8.10 minutes for the trans isomer, with a ratio between the cis isomer and the trans isomer of 20:80. The yield was 68.9.6%. The liquid crystal temperature range was found to be C0.2 (N)-1.7I, i.e. a C—N transition temperature of 0.2° C. and an N—I transition temperature of 1.7° C. The results of IR analysis of the product are shown below.

IR (liquid film) $v_{max}$: 2918, 2852, 2098, 1612, 1512, 1244, 1051, 887, 822 cm$^{-1}$ Comparative Example 6

The general procedure of Comparative Example 1 was repeated using 4-(2-(p-ethoxyphenyl)ethyl-1-n-pentyl-1-phenyl-silacyclohexane, thereby obtaining a product as intended in Example 6. The product had a ratio between the cis isomer and the trans isomer of 81:19 at a yield as low as 13.5%, thus being unfavorable.

EXAMPLE 7

Preparation of trans, trans-2-fluoro-4-(4-n-pentyl-4-silacyclohexyl)-4'-(4-n-propylcyclohexyl)biphenyl The general procedure of Example 1 was repeated using 2-fluoro-4-(4-n-pentyl-4-phenyl-4-silacyclohexyl)-4'-(trans-4-n-propylcyclohexyl)biphenyl. When subjected to gas chromatography under conditions of heating at a constant temperature of 300° C., the resultant product had a retention time of 19.55 minutes for the cis isomer and a retention time of 20.25 minutes for the trans isomer, with a ratio between the cis isomer and the trans isomer of 11:89. The yield was 74.6%. The liquid crystal temperature range was found to be C79.0S95.0N 247.0I, i.e. a C—S transition temperature of 79.0° C., an S—N transition temperature of 95.0 and an N—I transition temperature of 247.0° C. The results of IR analysis of the product are shown below.

IR (liquid film) $v_{max}$: 2920, 2848, 2098, 1493, 1404, 1194, 987, 887, 812 cm$^{-1}$

Comparative Example 7

The general procedure of Comparative Example 1 was repeated using 2-fluoro-4-(4-n-pentyl-4-phenyl-4-silacyclohexyl)-4'(trans-4-n-propylcyclohexyl)biphenyl, thereby obtaining a product as intended in Example 7. The product had a ratio between the cis isomer and the trans isomer of 87:13 at a yield as low as 9.6%, thus being unfavorable.

EXAMPLE 8

Preparation of trans, trans-4-(4-methoxycyclohexyl)-n-propyl-1-silacyclohexane

The general procedure of Example 1 was repeated using 4-(trans-4-methoxycyclohexyl)-1-n-propyl-1-phenyl-1-silacyclohexane. When subjected to gas chromatography under conditions of heating from 200° C. to 300° C. at a rate of 10° C./minute, the resultant product had a retention time of 4.33 minutes for the cis isomer and a retention time of 4.47 minutes for the trans isomer, with a ratio between the cis isomer and the trans isomer of 19:81. The yield was 69.9%. The liquid crystal temperature range was found to be C<−60N−40.0I, i.e. a C—N transition temperature of lower than −60° C. and an N—I transition temperature of −40° C. The results of IR analysis of the product are shown below.

IR (liquid film) $v_{max}$: 2928, 2856, 2820, 2098, 1452, 1103, 989, 887, 843, 820 cm$^{-1}$

Comparative Example 8

The general procedure of Comparative Example 1 was repeated using 4-(trans-4-methoxycyclohexyl)-1-n-propyl-1-phenyl-1-silacyclohexane, thereby obtaining a product as intended in Example 8. The product had a ratio between the cis isomer and the trans isomer of 87:13 at a yield as low as 10.1%, thus being unfavorable.

EXAMPLE 9

Preparation of 4-(2-(trans-4-n-pentyl-4-silacyclohexyl)-ethyl)-3',4'-difluorobiphenyl.

The general procedure of Example 1 was repeated using 4-(2-(4-n-pentyl-4-phenyl-4-silacyclohexyl)ethyl)-3',4'-difluorobiphenyl. When subjected to gas chromatography under conditions of heating at a constant temperature of 300° C., the resultant product had a retention time of 5.43 minutes for the cis isomer and a retention time of 5.53 minutes for the trans isomer, with a ratio between the cis isomer and the trans isomer of 18:82. The yield was 70.2%. The liquid crystal temperature range was found to be C38.6N-58.2I, i.e. a C—N transition temperature of 38.6° C. and an N—I transition temperature of 58.2° C. The results of IR analysis of the product are shown below.

IR (liquid film) $v_{max}$: 2920, 2850, 2100, 1605, 1504, 1311, 1267, 814 cm$^{-1}$

Comparative Example 9

The general procedure of Comparative Example 1 was repeated using 4-(2-(4-n-pentyl-4-phenyl-4-silacyclohexyl)ethyl)-3',4'-difluorobiphenyl, thereby obtaining a product as intended in Example 9. The product had a ratio between the cis isomer and the trans isomer of 80:20 at a yield as low as 11.4%, thus being unfavorable.

Example 10

Preparation of trans, trans-4-(4-(4-n-propyl-4-silacyclohexyl)-cyclohexyl)-3',4'-difluorobiphenyl.

The general procedure of Example 1 was repeated using 4-(trans-4-(4-n-propyl-4-phenyl-4-silacyclohexyl)cyclohexyl)-3',4'-difluorobiphenyl. When subjected to gas chromatography under conditions of heating at a constant temperature of 300° C., the resultant product had a retention time of 21.23 minutes for the cis isomer and a retention time of 21.59 minutes for the trans isomer, with a ratio between the cis isomer and the trans isomer of 14:86. The yield was 71.1%. The liquid crystal temperature range was found to be C82.7S107.5N 229.1I, i.e. a C—S transition temperature of 82.7° C., an S—N transition temperature of 107.5° C. and an N—I transition temperature of 229.1° C. The results of IR analysis of the product are shown below.

IR (liquid film) $v_{max}$: 2916, 2848, 2104, 1533, 1506, 1279, 985, 845, 814 cm$^{-1}$

Comparative Example 10

The general procedure of Comparative Example 1 was repeated using 4-(trans-4-(4-n-propyl-4-phenyl-4-silacyclohexyl)cyclohexyl)-3',4'-difluorobiphenyl, thereby obtaining a product as intended in Example 10. The product had a ratio between the cis isomer and the trans isomer of 85:15 at a yield as low as 8.9%, thus being unfavorable.

EXAMPLE 11

Preparation of 4-(trans-4-n-pentyl-4-silacyclohexyl)-2',4''-difluoroterphenyl

The general procedure of Example 1 was repeated using 4-(4-n-pentyl-4-phenyl-4-silacyclohexyl)-2',4''-difluoroterphenyl. When subjected to gas chromatography under conditions of heating at a constant temperature of 300° C., the resultant product had a retention time of 11.78 minutes for the cis isomer and a retention time of 12.67 minutes for the trans isomer, with a ratio between the cis isomer and the trans isomer of 10:90. The yield was 73.1%. The liquid crystal temperature range was found to be C87.8S135.0N 250.3I, i.e. a C—S transition temperature of 87.8° C., an S—N transition temperature of 135.0° C. and an N—I transition temperature of 250.3° C. The results of IR analysis of the product are shown below.

IR (KBr disc) $v_{max}$: 2918, 2846, 2106, 1487, 1223, 887, 816 cm$^{-1}$

Comparative Example 11

The general procedure of Comparative Example 1 was repeated using 4-(4-n-pentyl-4-phenyl-4-silacyclohexyl)-2',4''-difluoroterphenyl, thereby obtaining a product as intended in Example 11. The product had a ratio between the cis isomer and the trans isomer of 89:11 at a yield as low as 7.3%, thus being unfavorable.

EXAMPLE 12

Preparation of trans-4-(4-n-pentyl-4-silacyclohexyl)-2-fluoro-4'-(2-(3,4-difluorophenyl)ethyl)biphenyl The general procedure of Example 1 was repeated using 4-(4-n-pentyl-4-phenyl-4-silacyclohexyl)-2-fluoro-4'-(2-(3,4-difluorophenyl)ethyl)biphenyl. When subjected to gas chromatography under conditions of heating at a constant temperature of 300° C., the resultant product had a retention time of 15.89 minutes for the cis isomer and a retention time of 17.18 minutes for the trans isomer, with a ratio between the cis isomer and the trans isomer of 11:89. The yield was 72.8%. The liquid crystal temperature range was found to be C49.5(SA)50.6N 150.5I, i.e. a C—(SA) transition temperature of 49.5° C., an (SA)-N transition temperature of 50.6° C. and an N—I transition temperature of 150.5° C. The results of IR analysis of the product are shown below.

IR (KBr disc) $v_{max}$: 2920, 2102, 1518, 1491, 1404, 1290, 1286, 1120, 889, 818 cm$^{-1}$ Comparative Example 12

The general procedure of Comparative Example 1 was repeated using 4-(4-n-pentyl-4-phenyl-4-silacyclohexyl)-2-fluoro-4'-(2-(3,4-difluorophenyl)ethyl)biphenyl, thereby obtaining a product as intended in Example 12. The product had a ratio between the cis isomer and the trans isomer of 89:11 at a yield as low as 7.5%, thus being unfavorable.

EXAMPLE 13

Preparation of trans, trans-4-(2-(4-(4-n-propyl-4-silacylohexyl)cyclohexyl)ethyl)-4'-chloro-3'-fluorobiphenyl The general procedure of Example 1 was repeated using 4-(2-(trans-4-(4-n-propyl-4-phenyl-4-silacyclohexyl)cyclohexyl)ethyl)-4'-chloro-3'-fluorobiphenyl. When subjected to gas chromatography under conditions of heating at a constant temperature of 300° C., the resultant product had a retention time of 17.35 minutes for the cis isomer and a retention time of 18.39 minutes for the trans isomer, with a ratio between the cis isomer and the trans isomer of 14:86. The yield was 70.1%. The liquid crystal temperature range was found to be C63.3N208.0I, i.e. a C—N transition temperature of 63.3° C. and an N—I transition temperature of 209.0° C. The results of IR analysis of the product are shown below.

IR (liquid film) $v_{max}$: 2920, 2850, 2096, 1560, 1481, 1200, 1070, 982, 889, 845, 805 cm$^{-1}$ Comparative Example 13

The general procedure of Comparative Example 1 was repeated using 4-(2-(trans-4-(4-n-propyl-4-phenyl-4-silacyclohexyl)cyclohexyl)ethyl-4'-chloro-3'-fluorobiphenyl, thereby obtaining a product as intended in Example 13. The product had a ratio between the cis isomer and the trans isomer of 89:16 at a yield as low as 10.4%, thus being unfavorable.

EXAMPLE 14

Preparation of 4-(2-(trans-(4-n-pentyl-4-silacylohexyl)ethyl)-4'-(4-fluorophenyl)biphenyl The general procedure of Example 1 was repeated using 4-(2-(4-n-pentyl-4-phenyl-4-silacylohexy)ethyl-4'(4-fluorophenyl)biphenyl. When subjected to gas chromatography under conditions of heating at a constant temperature of 300° C., the resultant product had a retention time of 18.91 minutes for the cis isomer and a retention time of 19.45 minutes for the trans isomer, with a ratio between the cis isomer and the trans isomer of 17:83. The yield was 71.6%.

Comparative Example 14

The general procedure of Comparative Example 1 was repeated using 4-(2-(4-n-pentyl-4-phenyl-4-silacylohexyl)ethyl)-4'-(4-fluorophenyl)biphenyl, thereby obtaining a product as intended in Example 14. The product had a ratio between the cis isomer and the trans isomer of 80:20 at a yield as low as 14.2%, thus being unfavorable.

EXAMPLE 15

Preparation of 4-(trans-4-(trans-4-n-pentyl-4-silacyclohexyl)cyclohexyl)-1-trifluoromethoxybenzene The general procedure of Example 1 was repeated using 4-(trans-4-(4-n-pentyl-4-phenyl-4-silacyclohexyl)cyclohexyl)-1-trifluoromethoxybenzene. When subjected to gas chromatography under conditions of heating from 200° C. to 300° C. at a rate of 10° C./minute, the resultant product had a retention time of 9.28 minutes for the cis isomer and a retention time of 9.58 minutes for the trans isomer, with a ratio between the cis isomer and the trans isomer of 18:82. The yield was 68.8%. The liquid crystal temperature range was found to be C37.7N80.1I, i.e. a C—N transition temperature of 37.7° C. and an N—I transition temperature of 80.1° C. The results of IR analysis of the product are shown below.

IR (KBr, disc) $v_{max}$: 2924, 2854, 2102, 1510, 1267, 1223, 1194, 1154, 987, 818 cm$^{-1}$ Comparative Example 15

The general procedure of Comparative Example 1 was repeated using 4-(trans-4-(4-n-pentyl-4-phenyl-4-silacyclohexyl)cyclohexyl)-1-trifluoromethoxybenzene, thereby obtaining a product as intended in Example 15. The product had a ratio between the cis isomer and the trans isomer of 82:18 at a yield as low as 13.9%, thus being unfavorable.

As will be apparent from the foregoing example, the process of the invention is effective in selectively, preferentially preparing trans isomers of silacyclohexane compounds having a silicon atom in the molecule. The trans isomers exhibit good liquid crystal properties. The thus obtained silacyclohexane liquid crystal compounds are very valuable as a material for liquid crystal display devices.

What is claimed is:

1. A process for preparing a silacyclohexane compound which comprises the steps of:

(1) subjecting a compound of the following general formula (1)

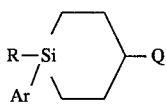 (1)

wherein Ar represents a phenyl group or a tolyl group, R represents a linear alkyl group having from 1 to 10 carbon atoms, a branched alkyl group having from 3 to 8 carbon atoms, a mono or difluoroalkyl group having from 1 to 10 carbon atoms, or an alkoxyalkyl group having from 2 to 7 carbon atoms, and Q represents a group of the following general formula (2)

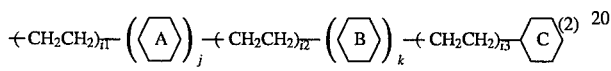 (2)

wherein 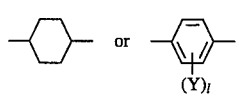 independently represent

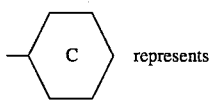

in which Y represents H, F or methyl and $l$ is a value of 0, 1 or 2, and

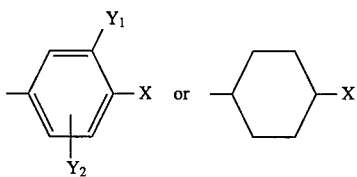 represents in which each X represents CN, F, Cl, $CF_3$, $CF_2Cl$, $OCF_3$, $OCHF_2$, $OCF_2Cl$, $OCHFCl$, $(O)_m CY_3 = CX_1 X_2$ wherein m is 0 or 1, $Y_3$ and $X_1$ independently represent H, F or Cl, $X_2$ represents F or Cl, $O(CH_2)_r(CF_2)_s X_3$ wherein r and s are, respectively, a value of 0, 1 or 2 provided that r+s=2, 3 or 4, $X_3$ represents F or Cl, or R or OR wherein R has the same meaning as defined above, i1, i2 and i3 are, respectively, a value of 0 or 1 provided that i1+i2+i3=1, and j and k are, respectively, a value of 0, 1 or 2 provided that j+k=0, 1 or 2, $Y_1$ and $Y_2$ independently represent H, F or Cl, to reaction with an electrophilic reagent comprising a halogen atom for conversion into a halosilacyclohexane compound of the following general formula (3)

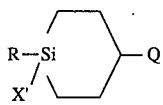 (3)

wherein R and Q have, respectively, the same meanings as defined above, and X' represents, F, Cl, Br or I;

(2) further reacting the halosilacyclohexane compound with an alcohol of the general formula, R'OH, wherein R' represents a linear alkyl group having from 1 to 10 carbon atoms or a branched alkyl group having from 3 to 8 carbon atoms to obtain an alkoxysilacyclohexane of the following general formula (4) wherein the steric configuration of the group, R, is equilibrated on the silicon atom

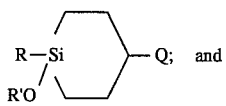 (4)

(3) subjecting the alkoxysilacyclohexane to reduction to obtain a silacyalohexane compound of the following general formula (5)

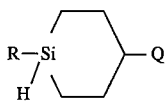 (5)

2. A process according to claim 1, wherein in step (2), the groups represented by R and Q are in a more stable trans configuration.

3. A process according to claim 1, further adding a lower alcohol or a metal alcoholate in step (2).

4. A process according to claim 1, further adding a neutralizing agent for a hydrogen halide secondarily produced during the reaction in step (2).

5. A process according to claim 1, further comprising subjecting the silacyclohexane compound obtained in step (3) to purification to obtain a trans form silacyclohexane compound.

* * * * *